US00PP32820P2

(12) United States Plant Patent
Ruter

(10) Patent No.: US PP32,820 P2
(45) Date of Patent: Feb. 16, 2021

(54) HOLLY PLANT NAMED 'RUTHOL2'

(50) Latin Name: ***Ilex crenata* x *I. maximowicziana***
Varietal Denomination: RutHol2

(71) Applicant: University of Georgia Research Foundation, Inc., Athens, GA (US)

(72) Inventor: John M. Ruter, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/602,829

(22) Filed: Dec. 5, 2019

(51) Int. Cl.
*A01H 5/12* (2018.01)
*A01H 6/00* (2018.01)

(52) U.S. Cl.
USPC ..... Plt./247

(58) Field of Classification Search
USPC ..... Plt./247
CPC ..... A01H 5/12; A01H 5/02; A01H 6/00
See application file for complete search history.

*Primary Examiner* — Keith O. Robinson
(74) *Attorney, Agent, or Firm* — Klarquist Sparkman, LLP

(57) ABSTRACT

A new cultivar of *Ilex* plant named 'RutHol2' is characterized by a combination of its compact, rounded growth habit, its resistance to damage from spider mites, its need for little pruning, its burgundy color new growth, and its ability to be used in large containers with other plants.

2 Drawing Sheets

Genus and species: *Ilex crenata* x *I. maximowicziana.*

Variety denomination: The new *Ilex crenata* x *I. maximowicziana* claimed is of the cultivar denominated 'RutHol2'.

BACKGROUND OF THE INVENTION

The present invention relates to a new and distinct cultivar of a Japanese holly plant named 'RutHol2'. Seed was collected from an unnamed F1 seedling (female) from the original cross of *Ilex crenata* 'Sky Pencil' (unpatented female) x *I. maximowicziana* #10-8S (unpatented male parent) plant.

The new 'RutHol2' variety is a product of a planned breeding program conducted by the inventor (in Watkinsville, Ga.). The objective of the *Ilex* breeding program is to create new plant cultivars with novel forms of growth, good cold hardiness, and resistance to damage from spider mites, insects and diseases.

The new 'RutHol2' plant is thus a product of *Ilex crenata* x *Ilex maximowicziana* F1 seedlings. The cross was made in 2010. The collected seed was sown in fall of 2010 and 276 seedlings were taken to a research nursery in Dearing, Ga. in spring of 2012. 'RutHol2', one of the plants grown from the collected seed, was selected for further evaluation in summer of 2014. 'RutHol2' has been evaluated for container production since 2012.

'RutHol2' has been evaluated through trials at a horticultural farm in Watkinsville, Ga. from 2016.

Asexual reproduction of the new 'RutHol2' variety was by vegetative terminal cuttings in a controlled environment in Dearing, Ga. and Watkinsville, Ga. since 2014. Observations of the new variety have shown that the unique features of this new 'RutHol2' are stable and have reproduced true to type in successive generations.

SUMMARY OF THE INVENTION

The cultivar 'RutHol2' has not been observed under all possible environmental conditions. The phenotype may vary somewhat with variations in environment and cultural practices such as temperature and light intensity without, however, any variance in genotype.

The following traits represent the distinguishing characteristics of the new cultivar. In combination, these traits set 'RutHol2' apart from all other existing varieties of *Ilex* known to the inventor.

1. 'RutHol2' has a compact, rounded growth habit
2. 'RutHol2' produces new growth that is burgundy in color
3. 'RutHol2' exhibits resistance to damage from spider mites
4. 'RutHol2' is an excellent foundation plant that requires little pruning
5. 'RutHol2' is very good for use in large containers with other plants

BRIEF DESCRIPTION OF THE FIGURES

The accompanying colored photographic illustrations show the overall appearance and distinct characteristics of the new 'RutHol2' variety. The colors in the photographs are as close as possible with the photographic and printing technology utilized.

The photograph labeled

The photograph labeled

COMPARISON WITH OTHER VARIETIES

Figure 1:
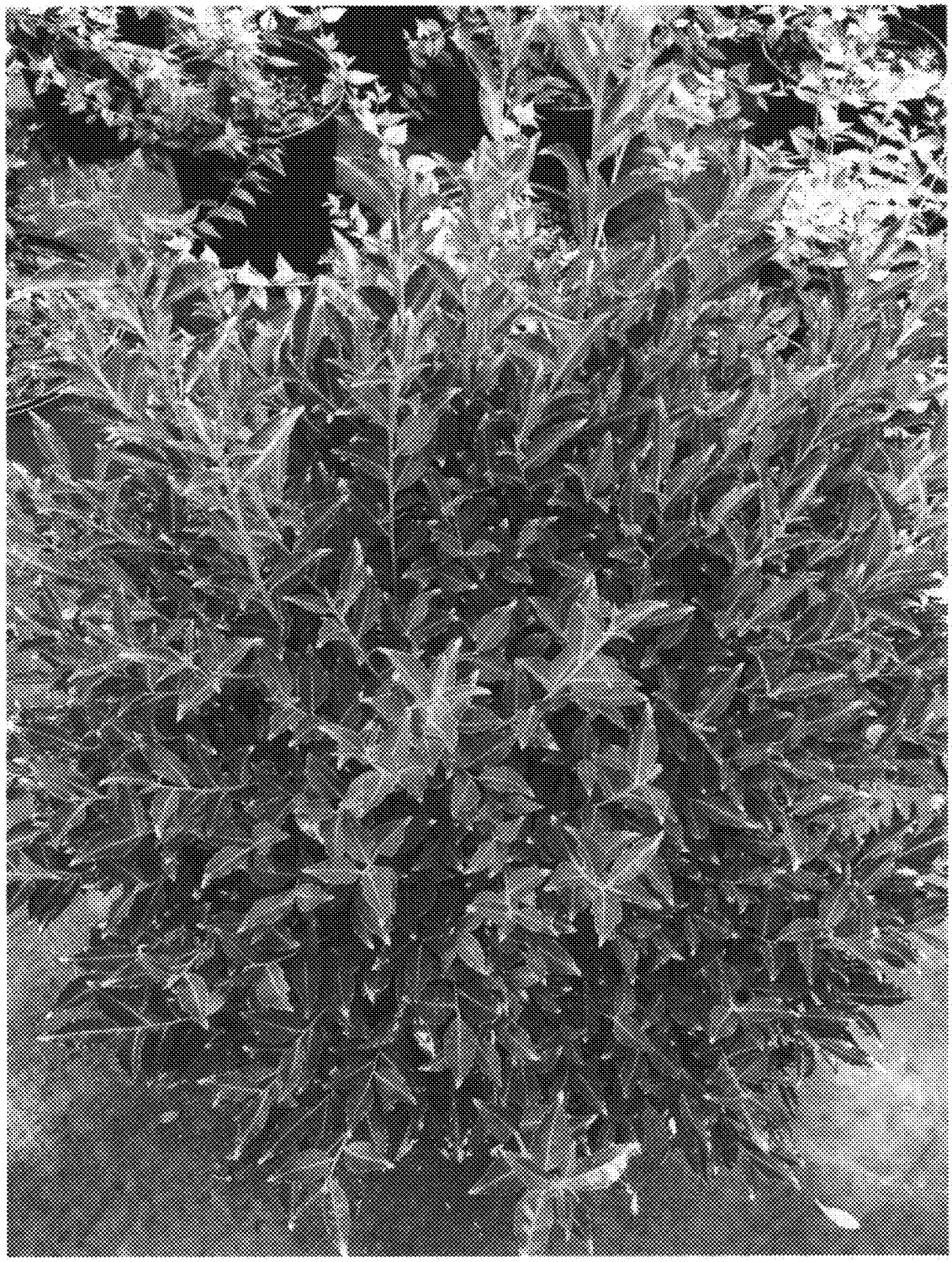
FIG. 1 is a photograph of a three year old (three years from cutting) 'RutHol2' plant and depicts the overall plant habit of 'RutHol2'.
Figure 2:
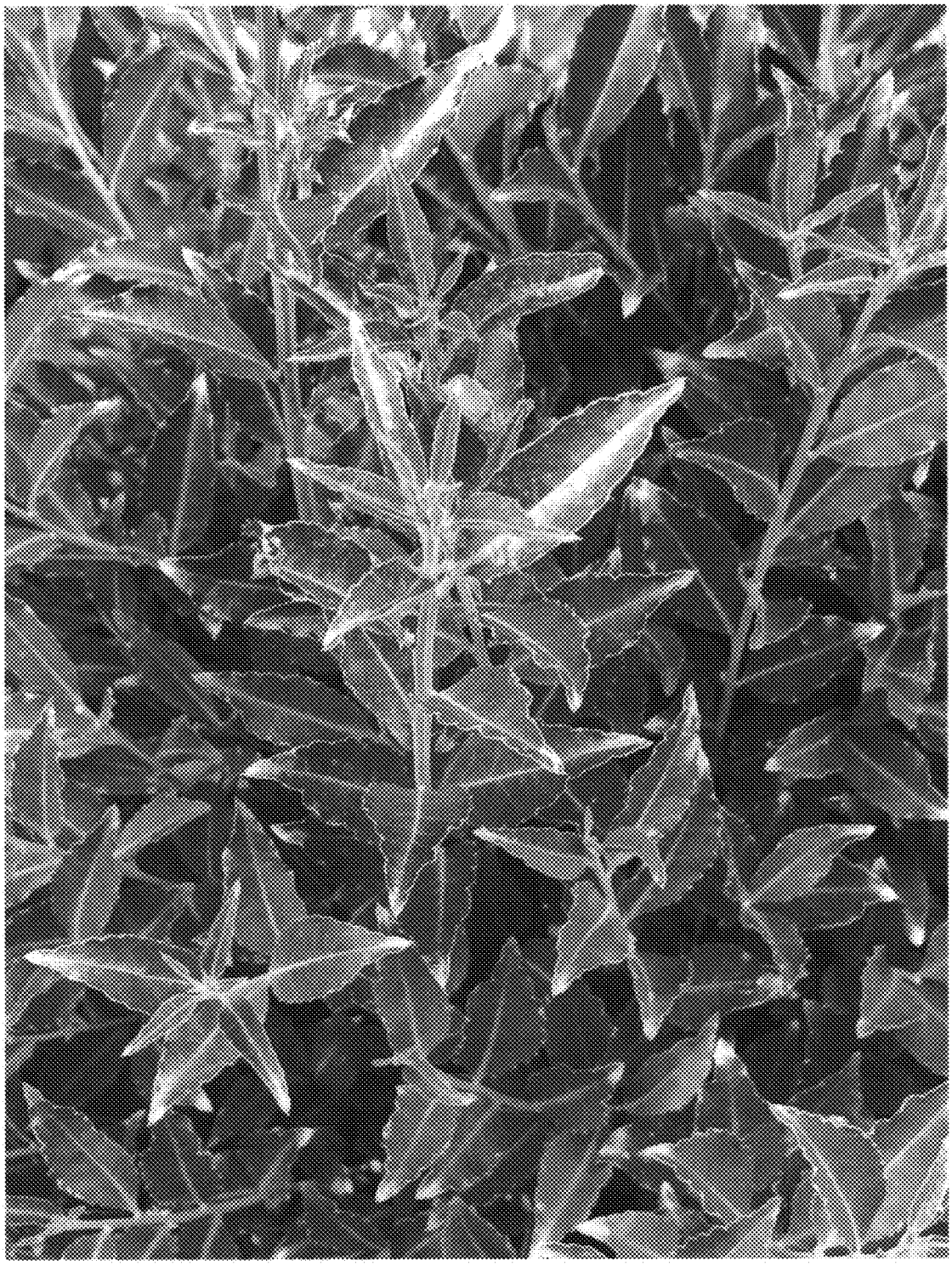
FIG. 2 depicts a close-up view of a portion of the foliage of the 'RutHol2' plant of FIG. 1.

The new 'RutHol2' is a male plant, while, in contrast, *Ilex crenata* 'Sky Pencil' is a female plant. 'RutHol2' is a slower growing plant than 'Sky Pencil'. In one growing trial, four year old (from cutting) 'RutHol2' plants growing in the ground averaged about 81 cm high, while five year old 'Sky Pencil' plants averaged about 117 cm high. The height to width ratio of *Ilex crenata* 'Sky Pencil' (typical ratio 3.9) and *Ilex maximowicziana* #10-8S (unpatented, typical ratio 1.5) is greater than the height to with ratio of 'RutHol2' (typical ratio 1.0). The leaves of the new plant are typically from 2.5 cm to 3.0 cm long in comparison to leaves of 'Sky Pencil' which are typically 2 cm to 3 cm long. The leaves of 'Ruthol1' (U.S. Plant Pat. No. 23,905) are typically 3.5 to 4.0 cm long and 'Ruthol1' has a greater height to width ratio.

DETAILED BOTANICAL DESCRIPTION

The following is a detailed description of the *Ilex* cultivar named 'RutHol2'. Data was collected at a horticultural farm at Watkinsville, Ga. from 3 year old plants grown outdoors in containers. Throughout this specification, color names beginning with a small letter signify that the name of that color, as used in common speech, where aptly descriptive. Color names beginning with a capital letter designate values based upon The R.H.S. Colour Chart, 6$^{th}$ edition published in 2015 by The Royal Horticultural Society (R.H.S.), London, England.

Parentage:

*Female parent.*—*Ilex crenata* 'Sky Pencil' x *Ilex maximowicziana* (female).

*Male parent.*—*Ilex crenata* 'Sky Pencil' x *Ilex maximowicziana* (male).

Habit: Compact, rounded evergreen shrub.

Size of plant: 3-gal. plant 4 years from cutting.

A. *Height.*—76 cm.

B. *Width.*—67 cm.

Stem:

A. *Color.*—Yellow-Green 144A.

B. *Length.*—5-30 cm.

C. *Diameter.*—2 mm.

D. *Texture/pubescence.*—Slightly hispid.

E. *Shape.*—Ridged, 5-sided.

F. *Odor* (*of bruised stem*).—None.

G. *Internode length.*—0.5-2.5 cm.

H. *Strength.*—Medium.

I. *Branches.*—5-10 main branches with 50-100 lateral branches.

Leaf:

A. *Type.*—Simple.

B. *Color* (*R.H.S.*).—1. Upper leaf surface: Emerging leaves — Greyed-Orange 166A. Mature leaves — Yellow-Green 147A. 2. Lower leaf surface: Emerging leaves — Grey-Brown 199A. Mature leaves — Green 137B.

C. *Mature size* (*l*×*w*): 2.5-3 cm×1 cm (average).

D. *Apex.*—Acute.

E. *Base.*—Cuneate.

F. *Margin.*—Serrulate.

G. *Shape.*—Elliptical.

H. *Lobes* (*present/absent*).—Absent.

I. *Texture/pubescence.*—Smooth, no pubescence (both surfaces).

J. *Arrangement on stem.*—Alternate.

K. *Venation.*—Pinnate.

L. *Texture.*—Leathery.

M. *Aspect.*—30-45°.

N. *Odor when crushed.*—None.

O. *Leaves per lateral branch.*—10-30.

Petiole:

A. *Length.*—4-5 mm.

B. *Shape.*—Hastate.

C. *Color* (*R.H.S.*).—Yellow-Green 144A.

D. *Texture/pubescence.*—Slightly hispid.

E. *Diameter.*—1 mm.

Inflorescence:

A. *Type.*—Solitary — usually single, occasionally in clusters of 2.

B. *Number per plant.*—<5000.

Flower:

A. *Number per inflorescence.*—1 — male.

B. *Axillary or terminal.*—Axillary.

C. *Symmetry.*—Regular.

D. *Height and diameter* (*l*×*w*): 2 mm×4 mm.

E. *Fragrance.*—None.

F. *Bud.*—1. Size (L×W): 1.5 mm×1.5 mm. 2. Shape: Round. 3. Color (R.H.S.): Greyed-Yellow 162B. 4. Texture/Pubescence: No pubescence.

G. *Blooms.*—Late April to mid-May in Athens, Ga. 1. Longevity: 3-5 days.

H. *Petals.*—1. Number: 4. 2. Size (L×W): 2 mm×2 mm. 3. Shape: Obovate. 4. Apex: Round. 5. Base: Round. 6. Margin: Smooth, entire. 7. Color at Peak of Bloom (R.H.S.): Yellow-White 158A. 8. Texture/Pubescence: Smooth, no pubescence. 9. Arrangement: Solitary.

I. *Pedicels.*—1. Color (R.H.S.): Yellow-Green 144A. 2. Texture/Pubescence: Slightly pubescent. 3. Length: 2 mm. 4. Aspect: Erect. 5. Strength: Weak.

J. *Sepals.*—1. Number: 4. 2. Size (L×W): 1 mm×2 mm. 3. Shape: Cuspidate. 4. Texture/Pubescence: Smooth/no hairs. 5. Color (R.H.S.): Yellow Green 144A. 6. Apex: Round. 7. Base: Truncate. 8. Margin: Sinuate.

K. *Stamens.*—1. Number: 4. 2. Anther: a) Size (L×W): 1 mm×<1 mm. b) Shape: Conical. c) Color (R.H.S.): Brown 200D. d) Texture/Pubescence: Smooth, no pubescence. 3. Filament: a) Size (L×W): 1 mm×<0.5 mm. b) Color (R.H.S.): Yellow-White 158A. c) Texture/Pubescence: Smooth, no pubescence. 4. Pollen: Male plant. a) Quantity: Moderate. b) Color (R.H.S.): Yellow 11B.

Pest and disease resistance: Resistant to spider mites (*Tetranychus urticae*).

Hardiness: Not fully determined. The plants have been grown in USDA zone 8. Parental species have survived −5° F. with no damage in Blairsville, Ga.

What is claimed is:

1. A new and distinct cultivar of the *Ilex* plant named 'RutHol2' as illustrated and described herein.

* * * * *